United States Patent [19]

Yancey

[11] Patent Number: 5,576,780
[45] Date of Patent: Nov. 19, 1996

[54] METHOD FOR EVALUATION OF LENGTH OF FOCUS OF THE EYE

[75] Inventor: Don R. Yancey, Keaau, Hi.

[73] Assignee: Cain Research Pty. Ltd., Warriewood, Australia

[21] Appl. No.: 490,604

[22] Filed: Jun. 6, 1995

Related U.S. Application Data

[63] Continuation of Ser. No. 267,123, Jun. 27, 1994, and a continuation-in-part of Ser. No. 888,166, May 26, 1992, Pat. No. 5,329,322.

[51] Int. Cl.⁶ .................. A61B 3/10; A61B 3/14; A61B 3/00
[52] U.S. Cl. .................. 351/211; 351/209; 351/246
[58] Field of Search .................. 351/205, 208, 351/209, 210, 211, 218, 221, 246, 206; 354/62

[56] References Cited

U.S. PATENT DOCUMENTS

| | | | |
|---|---|---|---|
| 3,136,839 | 6/1964 | Safir | 351/214 |
| 3,524,702 | 8/1970 | Bellows et al. | 351/205 |
| 3,525,565 | 8/1970 | O'Neill et al. | 351/211 |
| 3,536,383 | 10/1970 | Cornsweet et al. | 351/205 |
| 3,572,909 | 3/1971 | Vanpatten et al. | 351/205 |
| 3,598,107 | 8/1971 | Ishikawa et al. | 351/204 |
| 3,614,214 | 10/1971 | Cornsweet et al. | 351/205 |
| 3,623,799 | 11/1971 | Millodot | 351/222 |
| 3,663,098 | 5/1972 | Merchant | 351/205 |
| 3,715,166 | 2/1973 | Leighty et al. | 356/125 |
| 3,746,432 | 7/1973 | Mason | 351/205 |
| 3,791,719 | 2/1974 | Kratzer et al. | 351/211 |
| 3,819,256 | 6/1974 | Bellows et al. | 351/205 |
| 3,824,005 | 7/1974 | Woestman | 351/205 |
| 3,843,240 | 10/1974 | Cornsweet et al. | 351/200 |
| 3,880,501 | 4/1975 | Munnerlyn | 351/205 |
| 3,883,233 | 5/1975 | Guilino | 351/205 |
| 3,888,569 | 6/1975 | Munnerly et al. | 351/205 |
| 3,932,030 | 1/1976 | Hasegawa et al. | 351/221 |
| 3,992,087 | 11/1976 | Flom et al. | 351/205 |
| 4,007,980 | 2/1977 | Bracher et al. | 351/212 |
| 4,021,102 | 5/1977 | Iizuka | 351/205 |
| 4,105,303 | 8/1978 | Guyton | 351/205 |
| 4,277,150 | 7/1981 | Wada et al. | 351/205 |
| 4,293,198 | 10/1981 | Kohayakawa et al. | 351/211 |
| 4,293,199 | 10/1981 | Wada et al. | 351/205 |
| 4,304,468 | 12/1981 | Wada et al. | 351/205 |
| 4,306,778 | 12/1981 | Wada et al. | 351/211 |
| 4,315,672 | 2/1982 | Müller et al. | 351/13 |
| 4,353,625 | 10/1982 | Nohda et al. | 351/205 |
| 4,367,019 | 1/1983 | Kitao et al. | 351/211 |
| 4,372,655 | 2/1983 | Matsumura et al. | 351/206 |
| 4,376,573 | 3/1983 | Matsumura et al. | 351/212 |
| 4,390,255 | 6/1983 | Nohda et al. | 351/212 |
| 4,395,097 | 7/1983 | Mohrman | 351/201 |
| 4,408,847 | 10/1983 | Wada et al. | 351/205 |
| 4,421,391 | 12/1983 | Matsumura et al. | 351/211 |
| 4,591,247 | 5/1986 | Kamiya et al. | 351/211 |
| 4,650,301 | 3/1987 | Humphrey | 351/211 |
| 4,669,835 | 6/1987 | Humphrey | 351/205 |

(List continued on next page.)

FOREIGN PATENT DOCUMENTS

| 596749A1 | 5/1993 | European Pat. Off. . |
| 6311965A | 8/1994 | Japan . |
| 8606834 | 11/1986 | WIPO . |

Primary Examiner—Huy Mai
Attorney, Agent, or Firm—Brown, Martin, Haller & McClain

[57] ABSTRACT

An autorefractor utilizes two light emitters and corresponding optics to project images onto the fundus, with the focus of these images bracketing the gross sphere of an emmetrope. A single detector generates a signal corresponding to each emitter. In an alternate embodiment, a single emitter and two detectors having foci bracketing the gross sphere of an emmetrope generate a signal corresponding to each detector. The light reflected from the fundus is detected and the differential intensities of two signals are used to determine departure in refraction from 0 diopter sphere. Multi-segmented or CCD detectors may be used to measure cylinder/axis, determine length and direction of gaze (in combination with a Purkinje image sensor) and to generate and analyze retinal images.

8 Claims, 10 Drawing Sheets

U.S. PATENT DOCUMENTS

| | | | |
|---|---|---|---|
| 4,707,090 | 11/1987 | Humphrey | 351/205 |
| 4,730,917 | 3/1988 | Krueger | 351/211 |
| 4,744,648 | 5/1988 | Kato et al. | 351/211 |
| 4,859,051 | 8/1989 | Fukuma et al. | 351/211 |
| 5,011,276 | 4/1991 | Iwamoto | 351/211 |
| 5,157,427 | 10/1992 | Humphrey | 351/205 |
| 5,329,322 | 7/1994 | Yancy | 351/211 |

METHOD FOR EVALUATION OF LENGTH OF FOCUS OF THE EYE

This is a continuation of application Ser. No. 08/267,123, filed Jun. 27, 1994 pending and a continuation-in-part of application Ser. No. 07/888,166, filed May 26, 1992, now U.S. Pat. No. 5,329,322.

FIELD OF THE INVENTION

The invention relates to optical instruments for measuring refraction of the eye and specifically to an instrument for rapid objective refraction.

BACKGROUND OF THE INVENTION

Measuring the refraction of the eye is difficult as the eye is a living organ and is constantly changing and moving. Even with an intelligent and cooperative patient fixating a target, the eye will be moving because of micronystagmus. Without this constant motion, the eye cannot function. It is an established phenomenon that the eye is a differential sensing mechanism; if an image is perfectly fixed on the retina, the brain causes the image to fade from view. Thus, to see effectively, the eye must be constantly moving.

Alignment is a major problem for most methods of refraction. The optical axis of the eye must match the optical axis of the measuring instrument. Several methods of eye alignment have been used in the prior art.

One method to help ensure proper eye alignment is video imaging. Typically such video imaging enlarges the eye many times for display on a monitor so the examiner can determine that the eye is properly fixated and, hopefully, aligned.

A second method uses an eye tracker that follows the movement of the eye. Because of the double-pinhole principle used in most machines, alignment is critical.

In order to avoid the alignment problem, it has been known to use a measurement beam that over-fills the pupil so that alignment becomes less critical. However, a significant disadvantage of such instruments is that long measurement times (up to 20 seconds) are required to measure each eye.

Because the eye is constantly changing, measurements taken at different times can show different values due to random effects. The longer the time interval required for the measurement, the longer the integration of that measurement to previously obtained values. This is required to average out the random effects to improve the signal-to-noise ratio and, thereby, improve accuracy. One way to avoid movement errors is to have a very short measurement time, on the order of one millisecond. Unfortunately, random errors can appear in these short measurements.

The above problems of the measurement of refraction are compounded in the case of children. Objective refraction of children has always been associated with problems. Children have wide powers of accommodation such that conventional testing may obtain varied and inaccurate refractive readings. Further, children simply do not stay in the same place for overlong periods of time. Consequently, a different method of autorefraction is required. Finally, large and imposing optical apparatus—for example most conventional autorefractors—tend to excite and frighten the youthful subjects. This is especially true if the intimate presence of an operator proximate the child patient is required. Simply stated, the excited and frightened juvenile subject falsely accommodates—and the measurement of such refractions can be in error.

Accommodative error is the biggest problem in providing accurate and reproducible measurements. In order to see objects close-up, the lens of the eye must change shape, become "fatter" so that the nearby object will be clearly focused on the retina. Looking into a box, or any type of instrument, even when the object being viewed inside the box is at optical infinity induces accommodation. This is a psychological phenomenon. It has been discovered that when a subject looked through a small hole (such as a hole in a wall so that the subject thought he was looking into another room although the viewed object might be close by) caused accommodation to be relaxed.

Even older children—intelligent and trying to cooperate—because of lack of experience may not be able to readily position themselves in the chin/forehead rests, properly fixate the target, and remain still for the requisite measurement time. For infants and younger children refraction is even more difficult.

Bringing an instrument close to the child's eyes may cause the child to close his eyes and resist examination. In this case, measurement must be taken from a distance. One method of measuring from a distance of about one meter is using photorefraction techniques. Current instrumentation replaces photographic film with CCDs to get quick readouts. Nonetheless, no one has actually "solved" the problem of accommodation.

Three main methods used to relax accommodation (refraction is measured at optical infinity, "making" the eye change its optics to see a target at optical infinity) are the following: 1) having the patient fixate an object 5 meters or further away, 2) fixate a point of light or a "featureless" pattern, and 3) "fog" the eye with a positive lens so that accommodation causes the fixated target to become more blurred, thus encouraging relaxation of the accommodative mechanism.

The most commonly used method to relax accommodation is the fogging method. With a positive lens, the eye is refracted to get an initial reading. Then, an in-focus target such as a sailboat on the ocean, a tractor in a field, or a balloon in the sky, is presented to the patient, which is fogged to relax accommodation and get the patient's refractive reading. However, in cases of latent hyperopia in some children, fogging is not effective and a cycloplegia must be used to relax accommodation.

Another problem in providing accurate and reproducible refractions is that the basic meridional method of refraction requires great accuracy of the initial measurements. It can be mathematically shown that meridional error as little as one-quarter diopter can cause entirely erroneous results.

Meridional refraction requires a minimum of three meridional measurements, and these data are put into Lawrence's formula to calculate mean sphere, cylinder, and axis. If measurements are not accurate, as noted above, or if astigmatism is irregular, refraction can be in significant error. One approach to this problem is to search for the principal axes of astigmatism to provide better accuracy.

SUMMARY OF THE INVENTION

It is an advantage of the present invention to provide an instrument with which spherical measurement of the eye's fundus may quickly and directly obtained.

A further advantage of the invention is to provide an instrument that can measure the topological profile of the eye.

Another advantage of the present invention is to provide a method for determining astigmatism, cylinder and axis of the eye.

An additional advantage of the present invention is to provide a method for rapidly measuring length of gaze for interactive optics systems which further permits eye tracking and perimetry, and allows sharp images of the fundus of the eye to be generated.

In an exemplary embodiment, the autorefractor includes an optical path for interrogating the eye and an operator-to-patient eye sight path for initial gross instrument alignment. Once gross instrument alignment occurs, first and second images are projected by light emitters along the interrogating optical axis onto the fundus of the eye. These first and second images bracket the conventional prescription of an emmetrope by fixed diopter prescriptions (for example, bracketed by a −20 diopter image and a +20 diopter image). The light retro-reflected from the fundus is received at one or more detectors and light intensity from the two images is compared differentially to determine gross spherical prescription. Where a single detector is used, the light emitters are alternately pulsed to allow separation of the signals.

In another embodiment, a single emitter is used with the emitter projecting an image at or near 0 diopters in conjunction with two detectors which bracket 0 diopter, for example, having peak sensitivities at −20 diopter and +20 diopter. Here, only a single pulse is required to obtain measurement of refraction.

A vertex range sensor may be provided in the form of a single emitter and two detectors. This subsystem within the autorefractor detects gross alignment by summing the outputs of the two detectors such that when its signal varies the eye is not sufficiently aligned for accurate refraction.

A second embodiment of the vertex sensor uses the diopter measurement beams to determine vertex location by employing two, four, or any even multiple of two, photodetectors.

In an alternate embodiment, an emitter array with corresponding micro lens array may be provided to project to the eye, preferably on one identifiable side of the determined gross spherical prescription, to cover the central portion of the cornea with a preferably regular image array. A detector array with a corresponding micro lens array projects to a corresponding matrix on the eye and relays the images of the projected emitter array to a detector. At the detector, the intensity of the received interrogating image matrix is received and compared. On the detector array, telltale axial patterns co-incident to the principal axes of any astigmatic properties of the lens are created, including axis and power information.

A Purkinje imaging system may be included for precise instrument alignment. This system projects images along the interrogating optical axis of the instrument an includes a beam splitter operable in a discrete chromatic wave length (e.g., green). The projected images are examined through a detector for coincidence between the reflected Purkinje images of the optical interfaces of the cornea and front and back eye lens surfaces. A monitor detector detects image registration. This detector is coupled to a log amplifier for determining comparison of image intensity of all the respective Purkinje images whereby rapid indication of instrument alignment is signaled.

The Purkinje image sensor may also be used to track the direction in which the eye is looking, or the "direction of gaze". In this application, only the first Purkinje image is required, so relative image intensity is not critical.

While the following disclosed instrument is particularly useful with children due to the advantage of its compact size and maneuverability, the disclosed apparatus can be utilized with any person, and even animals. Among its numerous applications, the present invention can be used in scientific experiments at remote locations, for example, measuring refractive changes of astronauts' eyes in space, for rapid tracking of progress during laser refractive surgery, and for interactive control of virtual reality systems, to track the eye's focus and adjust the image focus accordingly. This latter technique may also used for diagnostic purposes by using charge-coupled device (CCD) detector arrays.

BRIEF DESCRIPTION OF THE DRAWINGS

Understanding of the present invention will be facilitated by consideration of the following detailed description of the preferred embodiments of the present invention, taken in conjunction with the accompanying drawings, in which like reference numerals refer to like parts and in which:

FIG. 3B is a diagrammatic view of the dual version of the invention having a calibration system incorporated therein.

DESCRIPTION OF THE PREFERRED EMBODIMENTS

Figure 1:
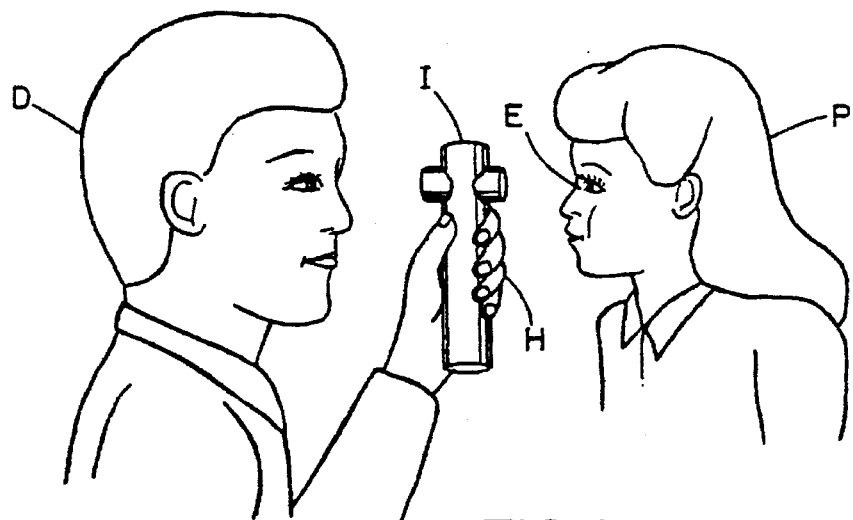
FIG. 1 is a perspective view of a child with an eye examiner holding the hand held instrument of this invention to the eye of a child for autorefraction of the child patient's prescription.

As illustrated in FIG. 1, an eye examiner D is shown holding instrument I of the present invention to eye E of patient P. As can be seen, instrument I is of a hand held variety and is held in hand H of eye examiner D during the objective refraction.

Figure 8:
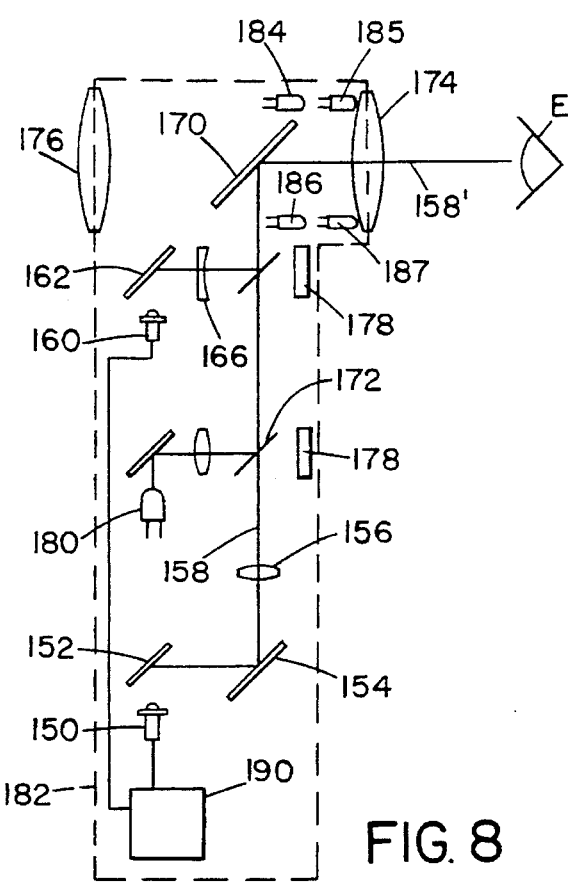
FIG. 8 is a diagrammatic view of the preferred embodiment of the invention.

The preferred embodiment of the present invention, shown in FIG. 8, has primary elements of two emitters 150 and 160, and photodetector 180, along with mirrors, beam splitters and lenses which transmit the incident and reflected light along optical path 158 to and from the subject's eye E. A viewer eyepiece 176 facilitates viewing of the eye E at a nominal vertex distance of 22 mm. A clocking device within the overall system processor 190, causes the emitters 150 and 160 to be alternately pulsed so that the photodetector 180 detects reflected light from one of the emitters at any given time. As will be explained in more detail below, the focus of the +D beam generated by emitter 150 is behind the retinal plane R of an emmetrope, while the −D beam from emitter 160 is focused forward of the retinal plane R.

The +D emitter 150, typically an LED, generates a beam carrying the image of the +D spot. First surface mirror 152 directs the +D beam to hot mirror 154, which transmits all light outside of the selected wavelength, in this case, 760 nm+30 nm, and reflects light within the selected range to follow optical path 158.

Lens 156 shortens the optical path and collimates the +D beam. Beam splitters 172 and 164 transmit the +D beam to hot mirror 170 which directs the beam through optometer lens 174 and into eye E.

The −Demitter 160 generates a beam carrying the −Dspot. The −D beam is reflected by first surface mirror 162 to beam splitter 164 to follow optical path 158. Hot mirror 170 directs the −D beam through optometer lens 174 and into eye E. It may be desirable to include an auxiliary lens within the −D beam subassembly to place it as close as possible to the optometer lens 174. The 0 diopter detector 180 may also require an auxiliary lens to shorten the optometer lens focal length and ensure the detector aperture is at 0 diopters.

Beam splitter 164 is not 50/50, i.e., it does not divide the beam equally in two directions. The +D beam passes through both beam splitters twice, while the −D beam passes through beam splitter 164 twice. Therefore, for maximum efficiency of the beam splitters should have reflection/transmission (R/T) ratios on the order of ⅓:⅔ for beam splitter 164 and 50:50 for beam splitter 172. Assuming the R/T to be correct, the intensity of the +D and −D beams should be equal at the eye. If not, the intensity differential can be corrected electronically or by using apertures.

Preferably, the focal points of the two beams should provide a minimal range of +/−13 diopters and up to +/−18 diopters, with an accuracy of 0.5 diopters. Ideally, the diopter range is +/−20 diopters.

In the prototype system, an infrared emitting diode manufactured by Hitachi (model HLP30R-A) was used. This LED provided favorable results because of its hemisphere-shaped active region such that the LED's internal connections would not be imaged. In order to avoid imaging of the LED internal connections in other types of emitters, and to compensate for differences in spot size from different emitters and optics, apertures may be used. The apertures must be selected to achieve efficient energy transfer while ensuring that +D and −D projected spots are equal in intensity.

The beam produced by the emitters is preferably on the order of 2.2 mm diameter so that small pupils do not obstruct the projected beams. This avoids reflected and diffused light from the cornea/iris. A larger beam diameter may be used so that the measurement beam overfills the pupil, but this may reduce signal-to-noise ratio.

The detector 180 is a photodiode selected to detect reflected light within the range of 760 nm±30 nm, although other wavelengths may be selected. The detector 180 is positioned in the optical path at a distance corresponding to "O"D, i.e., its focal point is at the retinal plane R of an emmetrope. For an emmetrope, the light of the two emitters reflected from the retinal plane will have equal intensity at the detector 180, as shown in FIG. 3B. If, however, there is a refractive error, the voltage supplied to the emitters (V1 to −Demitter, V2 to +D emitter) will be varied until equal intensity is measured at detector 180. The ratio of V1 to V2 will then correlate to refraction. It should be noted that the optical path is such that the emitters and detectors can be interchanged with no change in the geometric optics characteristics. More details of such a variation is provided below.

Figure 12:
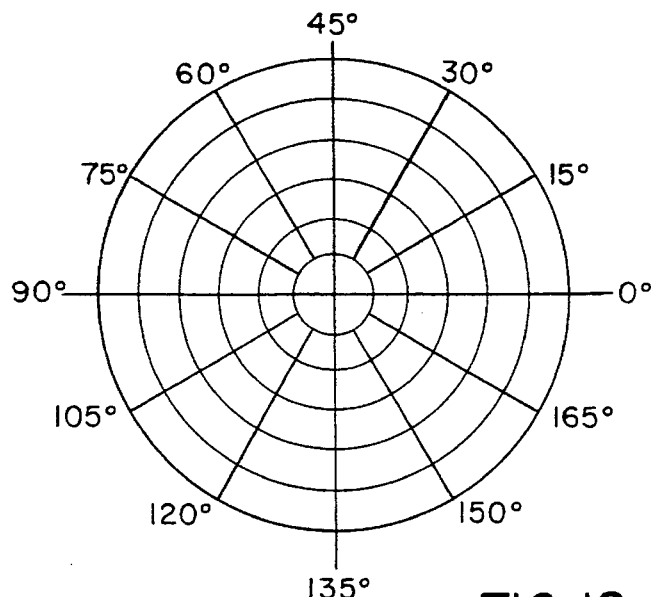
FIG. 12 is an exemplary prior art nomogram for meridional refractometry.

In the basic system, a single photodiode is used for detector 180. In the prototype, the photodiode was a Hamamatsu 1336–18B, with a sensitivity of 0.36 A/W at 700 nm and 0.50 A/W at peak. Other types of detectors may be used, including multi-segmented photodiodes and CCD imagers. Using CCD arrays also allows measurement of the deformation of the projected spot (or other shape image) to find the axis of deformation and amount of deformation to determine, empirically and using a look-up table, cylinder and axis (astigmatism) of the eye. Alternatively, the ratios of intensities reflected from preselected meridians can be used to determine distortion due to astigmatism. (FIG. 12 provides a typical nomogram for meridional refractometry, which is known in the art.)

By substituting CCD arrays in place of the discrete photodetectors, and such CCDs being unapertured, the ratio of the diameters of the detected +D image and −D image can be used to correlate to refraction.

Cylinder and axis can also be measured by substituting a multisegmented photodiode for the above-described detector 180. For complete determination of +/−diopter sphere, cylinder and axis, three meridians must be measured, meaning that a photodiode with at least six segments should be used. The nomogram of FIG. 12 provides an example of how pie-shaped segments can be defined. In the prototype system, an 8-segmented photodiode was preferred.

With the multi-segmented photodiode at the 0 D position, the signals from all segments corresponding to preselected meridians are summed to find +/−diopter sphere. The refraction of each meridian can then be found by sequential reading. By finding +/−D sphere and using high speed sampling of the meridians, the total measurement speed for a full refraction can be decreased by as much as 80% of that required for five sequential measurements. Cylinder/axis measurement can be performed by comparing intensity ratios across the meridians.

Figure 3A:
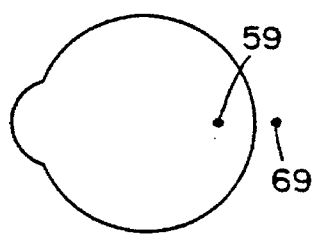
FIGS. 3A, 3C and 3E are schematics of a human eye in cross section illustrating focus of light to the surface of the retinal plane of respective emmetrope, hyperope and myope.
Figure 3C:
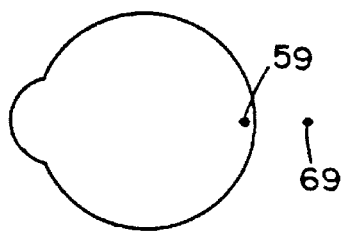
Figure 3E:
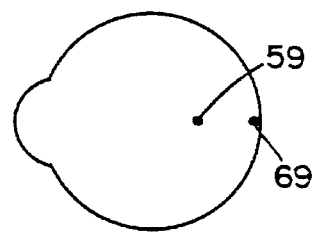
Figure 3B:
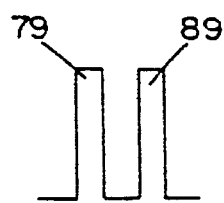
FIGS. 3B, 3D, and 3F are respective schematic signal intensity plots illustrating the operation of the objective refractor of this invention on each of the respective subjects.

Referring to FIGS. 3A and 3B, the case of the emmetrope is illustrated, with a signal generated by a single diode. Presuming that each of the respective light sources is focused with a twenty (20) diopter differential on the eye E of emmetrope for imaging at retinal plane R, it will be seen from FIG. 3B that the respective signals 79 from the −D spot 59 and signal 89 from the +D spot 69 will be approximately equal, i.e., the difference will be zero or near-zero. This is so because spots 59, 69 will be approximately equally out of focus with respect to retinal plane R.

Figure 3D:
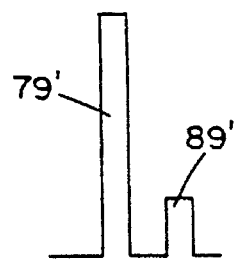

Referring to FIGS. 3C and 3D, the case of a hyperope is illustrated. Presuming that each of the respective light sources is focused with a twenty (20) diopter differential on the eye E of a hyperope for imaging at retinal plane R, it will be seen from FIG. 3D that the respective signal 79' from the −D spot 59 is intense. At the same time, signal 89' from the +D spot 69 will be diminished, resulting in a significant non-zero difference. This is the case because, with respect to retinal plane R, the +D spot 69 will be out of focus while the −D spot 59 will fall on retinal plane R. This example presumes pronounced hyperopia.

Figure 3F:
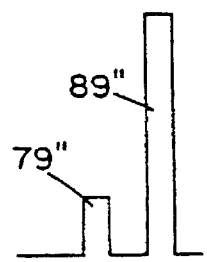

Referring to FIGS. 3E and 3F, the case of a myope is illustrated. Presuming that each of the respective light sources is focused with a twenty (20) diopter differential at the eye E of a myope for imaging at retinal plane R, it will be seen from FIG. 3D that the respective signal 79" from the −D spot 59 is diminished, so that the difference is, again, non-zero. At the same time signal 89" from the +D spot 69 will be intense. This occurs because, with respect to retinal plane R, the −D spot 59 will be out of focus while the +D spot 69 will fall on retinal plane R. This example assumes pronounced myopia.

Figure 14:
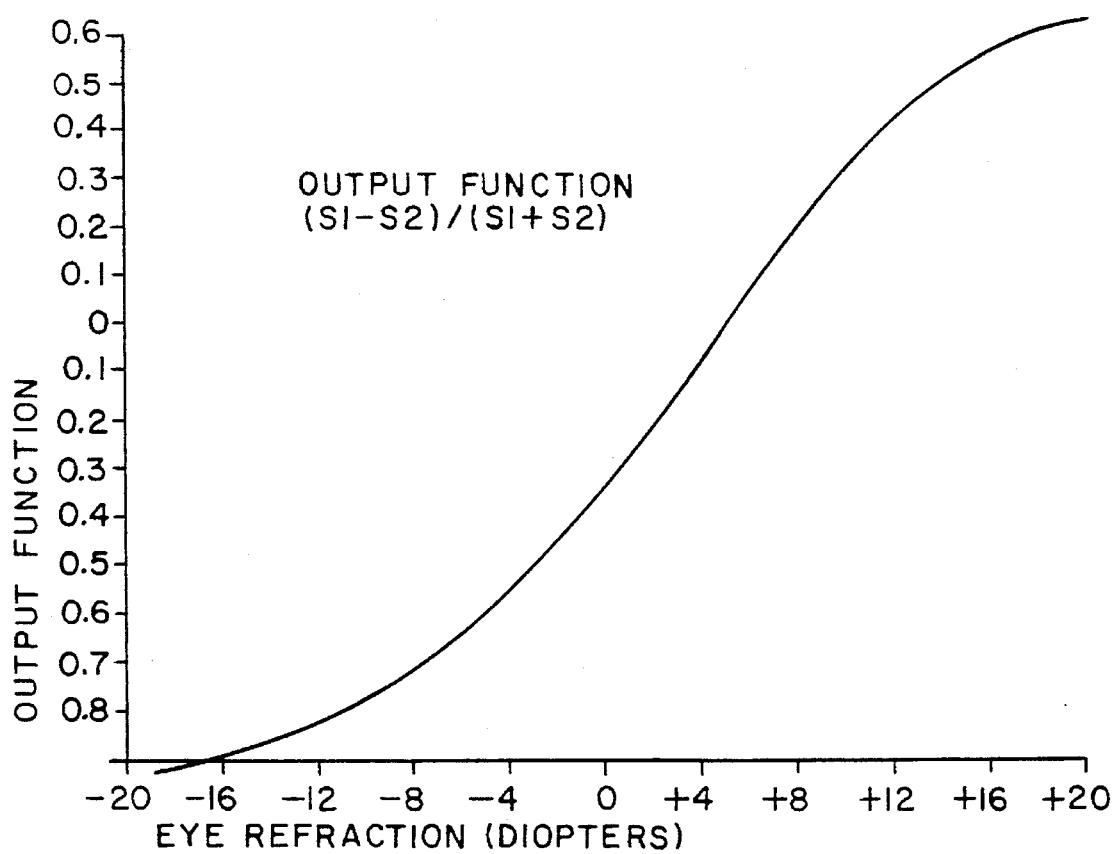
FIG. 14 is a plot of output function with eye refraction in diopters.

Referring to FIG. 14, the relationship between two projected spots, such as 59 and 69 in FIGS. 3A, 3C and 3E, is the corresponding retro-reflected detected intensities of the signals S1 and S2. In this case, signals S1 and S2 are generated by detector 180 from alternating illumination by emitters 150 and 160. The two detected signals S1 and S2 produce an output function that gives the corresponding eye refraction. This output function, shown by the curve in FIG. 14 for the sphere diopter refraction range of −20 to +20 diopters, is represented by the equation (S1−S2)/S1+S2).

The electronic circuitry is designed to obtain S1 and S2, and then signal processing calculates the equation (S1−S2)/(S1+S2) to provide the correlation to the +/− diopter sphere refraction of the eye. Note that many different circuits can be configured to obtain S1 and S2 and then calculate the given equation.

Determination of the intensities and relationships between the detected intensities can be achieved in a variety of ways, either directly or by using the output function. This relationship is then used to obtain the eye refraction.

Figure 9:
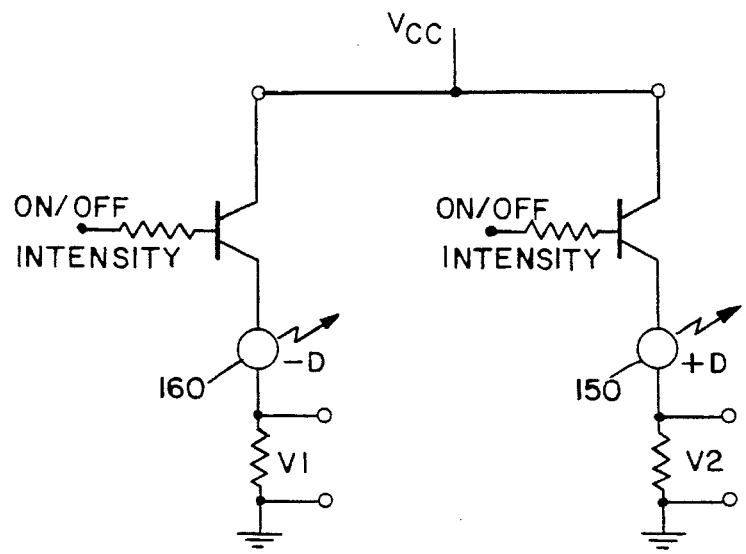
FIG. 9 is a simplified schematic of the illumination control circuitry of the preferred embodiment.

In the first embodiment, in order to determine the difference in intensities of light from emitter 150 and emitter 160 reflected from the fundus, activation of the emitters must be alternated so that detector 180 received each signal separately. This is accomplished by pulsing the emitters during alternating clock cycles, providing the current at nodes 191 and 192 to activate the appropriate emitter, as shown in FIG. 9. While variable resistors 194 and 196 are shown as controlling V1 and V2 respectively, variation of the intensity emitted by each emitter, or variation of the intensity as seen at the eye E, can also be achieved by automatic gain control (AGC) circuitry, digital control of pulsing, or by software, using an algorithm to enable usage of fixed-intensity emitters, all of which are known in the art. The detailed schematic of the control circuitry of the preferred embodiment, which will be understood by those skilled in the art and is explained below, is provided by FIG. 10.

Referring back to FIG. 8, housing 182 is generally the size of a small flashlight so that it can be held comfortably in the examiner's hand, as well as being carried easily in a pocket or small pouch. The various components of the system are mounted in slots within the housing to allow for quick and easy changing of lenses and other components.

Antireflection devices 178 are positioned in a horizontal line with beam splitters 164 and 172. These devices have black mirror surfaces rotated 90° to the corresponding beam splitter so that p or s polarized reflections cannot reflect back to the photodetector 180.

A vertex range sensor may also be included within the housing 182 for purposes of determining the optimal test distance range. This sensor consists of two photodetectors 184 and 186, which are positioned at narrow angles with respect to the optical path 158', and a single emitter, which can be either emitter 150, 160 or a separate dedicated IR emitter. The vertex sensors 184 and 186 have narrow optical acceptance angles so that light from the +D and −D beams are detected only when the eye is inside the acceptable vertex range of (nominal) 12 mm to 32 mm vertex distance. The outputs of the vertex sensors are summed and the summed values will remain constant as long as the eye is within the acceptable vertex range. When the summed value changes, the system processor can produce a visual or audible alarm signal to indicate that the instrument is not adequately aligned with the eye.

A second pair of detectors 185 and 187, positioned slightly outside of detectors 184 and 186, may be included to permit level control circuits to be used for the vertex range sensor. The outer detectors 185 and 187 can have wide acceptance angles while the inner detectors 184 and 186 have narrow acceptance ranges to more closely sense vertex distance of the eye. Also, because the detectors are paired and are positioned to span the center of the eye, equal signal strength and direction of gaze, as well as vertex distance can be monitored.

The inventive system operates to measure departure in refraction from a gross sphere by determining the ratio of the difference/sum components of the reflected light, i.e., the total and relative intensities of light detected by the detector(s). The difference/sum will vary with different subjects' eyes in overall magnitude as well as lens correction. Three different methods may be used to obtain the difference/sum components.

First, the illumination from each emitter can be maintained at a constant level, resulting in a sum component which is the function of both total reflection and differential reflection. This implies that a complete calculation of sum and difference be made as well as calculation of their ratio. For electrical implementation, the difference can be evaluated by measuring each section independently while the sum component is obtained by activating both emitters simultaneously.

The second method used feedback controlled emitter intensity to maintain a constant sum component at the amplifier output. The advantages of this techniques are that the power is held at the (arbitrary) minimum power necessary to maintain a good signal-to-noise ratio, and the division process is simplified since the divisor is constant.

The third method is a variation on the first. Here, separate measurements are made only for the two pulsed emitters, then the sum is derived electronically. This results in a one-third reduction in LED excitation current as compared to the first method.

The system of the present invention can operate in either a continuous or single step mode, with the continuous mode being reserved primarily for system diagnostics and demonstration. The single step mode is used for actual measurement. In the latter mode, the LED's are sequenced once, then the detected signal is processed and the resulting data is stored and/or displayed.

Figure 10:
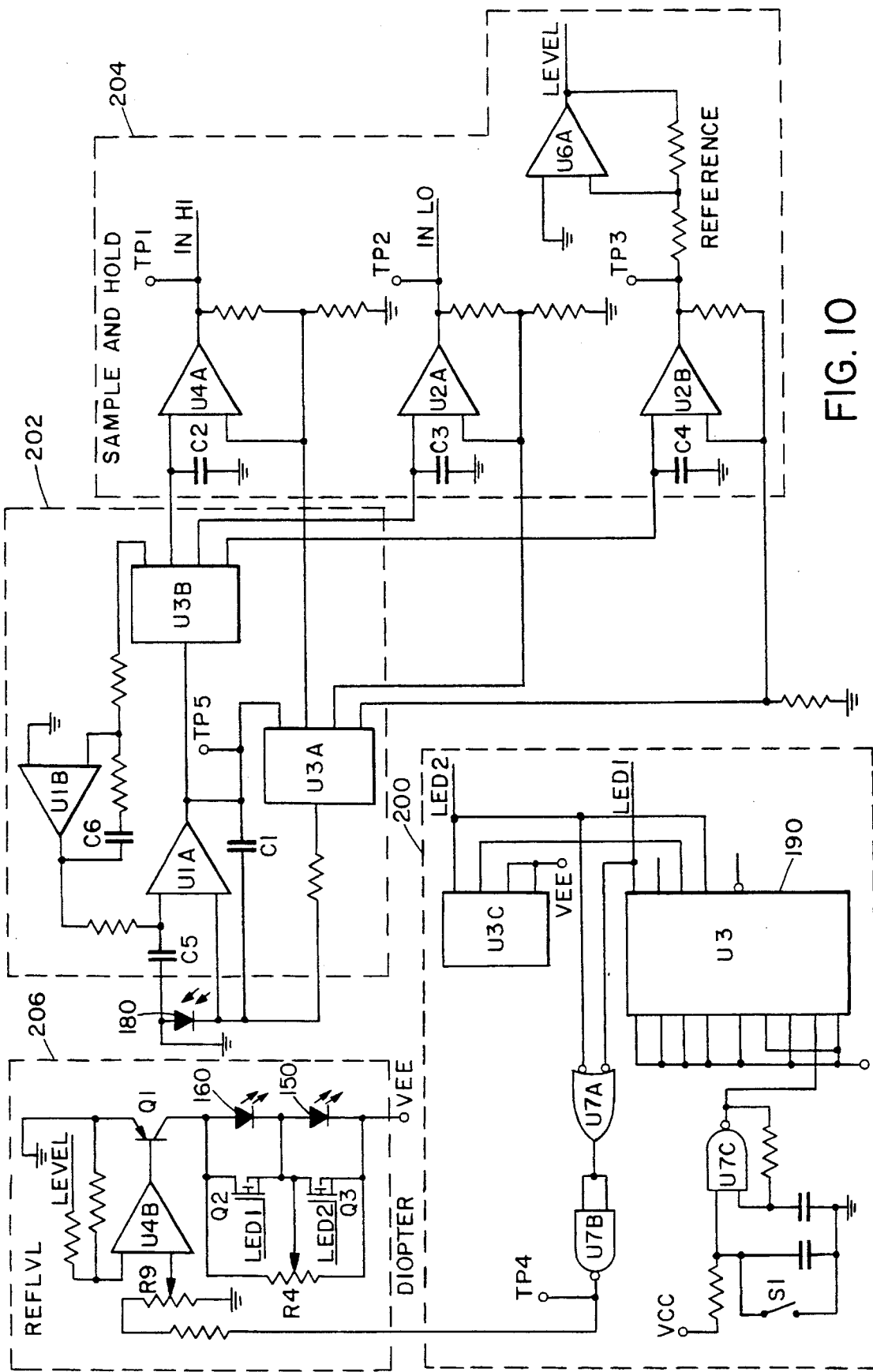
FIG. 10 is a simplified schematic of the control/detection circuitry of the preferred embodiment.

Referring to FIG. 10, the LEDs 160 and 150 are driven by a precision, adjustable current source and are switched on and off by logic signals LED1 and LED2 respectively. These logic signals are derived from the control logic circuit block 200 which also generates the timing signals for the auto-zeroed preamp block 202 and the sample-and-hold amplifier block 204.

The system control logic is implemented by U3A, U5 and U7A, B and C, all within block 200. The control logic includes a clock oscillator, divideby–16 ($\div 16$) timing counter and logical functions implementing LED and sample/hold control. It may also include circuitry for reduced body switch noise and control logic to select and set operating modes of either continuous, single step or standby/off.

The LED driver logic circuit 206 includes LED drive transistors Q1, Q2 and Q3. The LED current level is adjusted by REFLVL potentiometer R9 and maintained at the correct sum component level by feedback from the REFERENCE channel sample/hold amplifier U2B (LEVEL).

In the auto-zeroed preamplifier 202, the output from detector diode 180 (D3) is amplified by the transimpedance amplifier U1A. This amplifier obtains its feedback drive from the appropriate sample/hold through multiplexer U3A and U3B as determined by the clock generator and counter.

During one-fourth of the clock/counter cycle, both emitters 150 and 160 are off and the detector 180 is illuminated by ambient and stray light only. During this "auto-zero interval", U1B is connected in a closed loop feedback circuit to zero the amplifier output. This is accomplished by storing the required offset voltage on capacitor C6. After the auto-zero interval is completed, U1B maintains the offset voltage while the measuring cycle is completed.

The sample/hold logic is activated after the auto-zero cycle is complete, emitter 150 is turned on and emitter 160 is off. The signal representative of detected light obtained from the optical system is measured and stored on capacitor C2. The signal is then amplified by U4A (test point TP1). The output voltage is fed back through U4A, thus completing a precision closed-loop-feedback-controlled sample and hold function.

The above process is repeated in the next quarter clock cycle with emitter 160 off and emitter 150 on. This signal is stored on capacitor C3 and appears amplified at test point TP2. The difference voltage between TP1 and TP2 represents the difference component used for determining refraction.

During the next quarter cycle, both emitters 150 and 160 are on. The sum component generated by the detector 180 is stored on capacitor C4 and appears amplified at TP3. The sum component is further inverted and fed back (LEVEL) to the LED drive logic block 206. This feedback maintains the sum component at a constant level, thus eliminating the need to perform the calculation of the difference divided by the sum. In this case, the measured difference component is directly proportional to the actual reading because of the constant denominator.

The components of the inventive system can be operated to simulate the attenuation of a subject's eye to assist in set up. Emitters 150 and 160, and detector 180 are enclosed in a (partially) light-tight housing. The emitters are operated at low power (about 10–20 mA) and directed away from the detector. Internal reflection within the housing allows some of the light from each emitter to be detected, simulating an attenuation of about $10^{-4}$, or an optical density of 4, while the current provided to each emitter can be varied to simulate the refraction property. The potentiometer R4 connected across the emitters allows the current of one unit to be varied from full on to full off, while the other varies from off to on. Both emitters are full on when the potentiometer R4 is at the center of its range.

The prototype of the inventive system operates off of a $\pm 6$ V power supply. Current drain is approximately 20 mA. This power can be furnished from an 8-AA cell battery pack, with a center tap at the midpoint. The battery pack is preferably rechargeable, using, for example, Rayovac® reusable batteries sold under the name "Renewal Battery". Other types of batteries, which are known in the art, may be used.

The autorefractor of the present invention is best set up and demonstrated using a two channel oscilloscope to 1) adjust the emitter operating point to the correct value, and 2) to observe the effects of the DIOPTER control on the difference outputs and the sum (REFERENCE) component.

To adjust the sum level, one channel of the oscilloscope is connected to TP4, and sync to the positive transition. The oscilloscope is adjusted to obtain a single cycle. The positive pulse, from $-6$ V to $+6$ V represents the auto-zero interval. This is followed by three equal time intervals. The voltage at TP5 represents the amplified light signal during each interval. A transient due to the CMOS body switch parasitic may appear but can be ignored. The signal at TP5 is zero during the auto-zero interval, followed by the components due to emitter 160 and 150. The fourth interval shows the sum component, which can be adjusted using REFLVL to 2.0 V to demonstrate the system operation. This adjustment should be made with the DIOPTER adjustment centered such that the detector signals corresponding to emitters 150 and 160 outputs are equal. Under these conditions, emitters 150 and 160 should produce 1.0 V and the difference across TP1 and TP2 should be zero.

The eye characteristics to be tested by the present invention can be simulated by varying the differential intensity of the emitters. This must be done electronically since there are no mechanical components available to adjust these parameters. The modified relative intensities become an approximate simulation of operation of the inventive system, i.e., a condition has been created whereby the autorefractor can provide an indication of departure from gross sphere as represented by a differential in signal intensities received by the detector. Adjusting the DIOPTER potentiometer R4 varies the light intensity from maximum at balance to complete shut off of either leg. The REFERENCE level may vary up to a range of 2:1.

For set up, it may also be desirable to provide an offset for corneal reflection, which may be determined using off-axis measurement. The contribution of this component relative to the overall signal must be determined empirically under varied conditions, e.g., different background lighting, and on different subjects. This should enable greater accuracy and increased diopter range.

Figure 11:
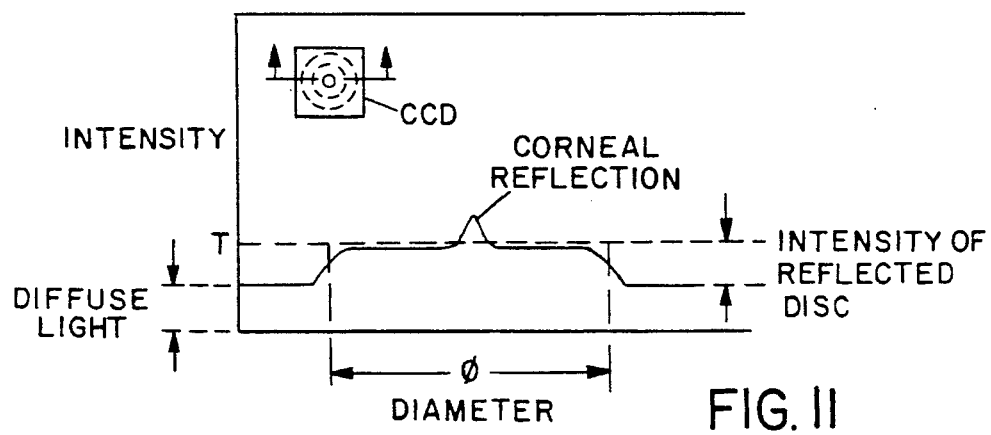
FIG. 11 is a plot of intensity of detected light across a CCD imager as used according to the present invention.

One method for removal of the corneal reflection component is to use a CCD detector to generate a cross-section of the intensities through all of the meridians. As illustrated in FIG. 11, the corneal reflection can be determined to be those readings which exceed a intensity threshold T. This value could then be inserted as a correction factor within the software which processes the signals.

Figure 13A:
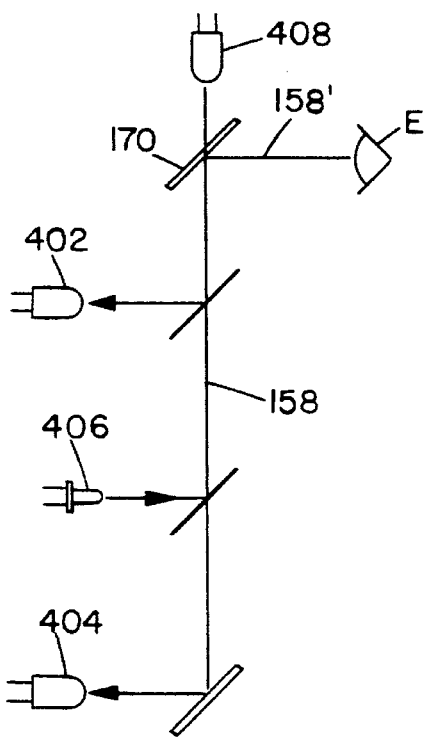
FIG. 13A is a diagrammatic view of the calibration system.

An alternate embodiment, illustrated in FIG. 13A, is a "dual version" of the first embodiment, "dual" referring to the use of two photodetectors 402 and 404 along with a single emitter 406 and their corresponding optics. In this case, signals S1 and S2 will be generated by the two separate detectors. As stated above, the construction of the invention allows detectors and emitters to be interchanged without requiring any changes to the geometric optics characteristics. Thus, substituting the dual version components into the structure described for the first embodiment as illustrated in FIG. 8, detector 404 is focussed, via its corresponding optics to the +D position (in place of emitter 150) and detector 402 is focussed to the −D position (in place of emitter 160). Emitter 406 (in place of detector 180) projects an image to the OD position., i.e., the retinal plane of an emmetrope. Thus, the focusses of the detectors bracket the OD position, for example, at +20/−20 diopter. In this version, a single pulse of emitter 406 will generate signals, when reflected, in both detectors. For an emmetrope, the detector signals S1 and S2 generated by detectors 402 and 404 will be equal. As in the previous embodiment, the relationship (S1−S2)/(S1+S2) is used to determine refraction.

In the dual version, for cylinder and axis measurement, the same procedure described above is employed, where the detectors are multi-segmented, except that each S1 and S2 corresponds to a meridian, and each meridian obtained from S1 and S2 detectors have at least six pairs of circularly-arranged segments corresponding to at least three meridians.

The prototype of the dual version uses a photodiode with 64 active areas arranged in a ¼ inch diameter circle, which corresponds to 32 pairs of segments and 32 meridians. However, every eight adjoining areas are connected to obtain four pairs of segments and four meridians.

As illustrated in FIG. 13A, the dual version may also include a third photodetector 408 to provide feedback control to ensure a constant illumination level. Illumination must be constant in order for the relationship (S1−S2)/(S1+S2) to conform to the output function described above. The use of a separate, third detector 408 is advantageous since it is placed outside of the optical path of the eye, and is, thus, independent of signals from the eye. In this case, hot mirror 170 needs to be "leaky", i.e., pass a portion of the light from emitter 406 to detector 408. The third detector 408 provides a reference signal to calibrate the system to ensure constant illumination to eliminate variations that may be introduced by heat and aging of the components.

Figure 13B:
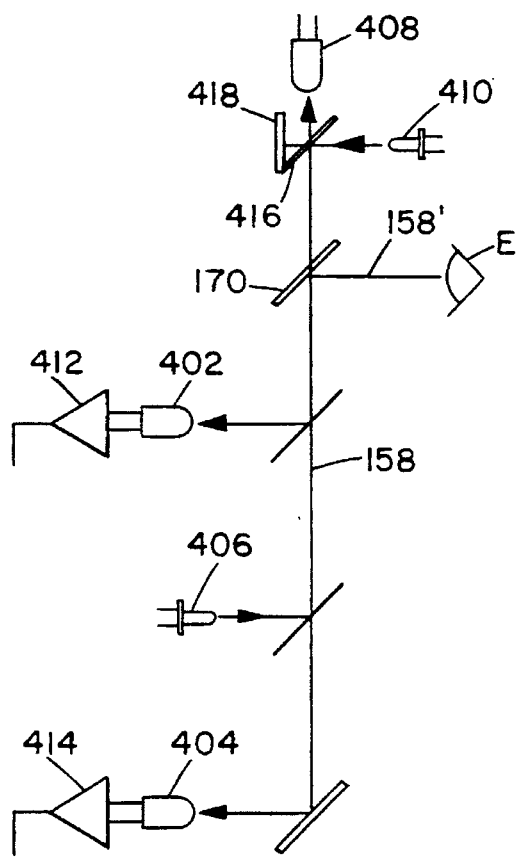

The third photodetector 408 may also be used in conjunction with a second emitter 410, shown in FIG. 13B. Second emitter 410, which is first calibrated by third detector 408, provides an independent light source for calibration of the two detectors 402 and 404. Specifically, detection of light from the independent second emitter provides a reference signal for matching the gains of the photoamplifiers 412 and 414 which amplify the signals S1 and S2 generated by the detectors 402 and 404, respectively. A beam splitter 416 splits light from emitter 410 between detector 408 and optical path 158 (with the exception of the portion 158' of the optical path which is downstream from hot mirror 170). The light from emitter 410 is directed to all three detectors. Black panel (or mirror) 418 reflects light passing through the front surface of beam splitter 416 back to the back surface of the beam splitter, then up into detector 408. First, detector 408 is used to calibrate the level of light output by emitter 410, then calibrated emitter 410 is used to calibrate detectors 402 and 404.

Figure 2:
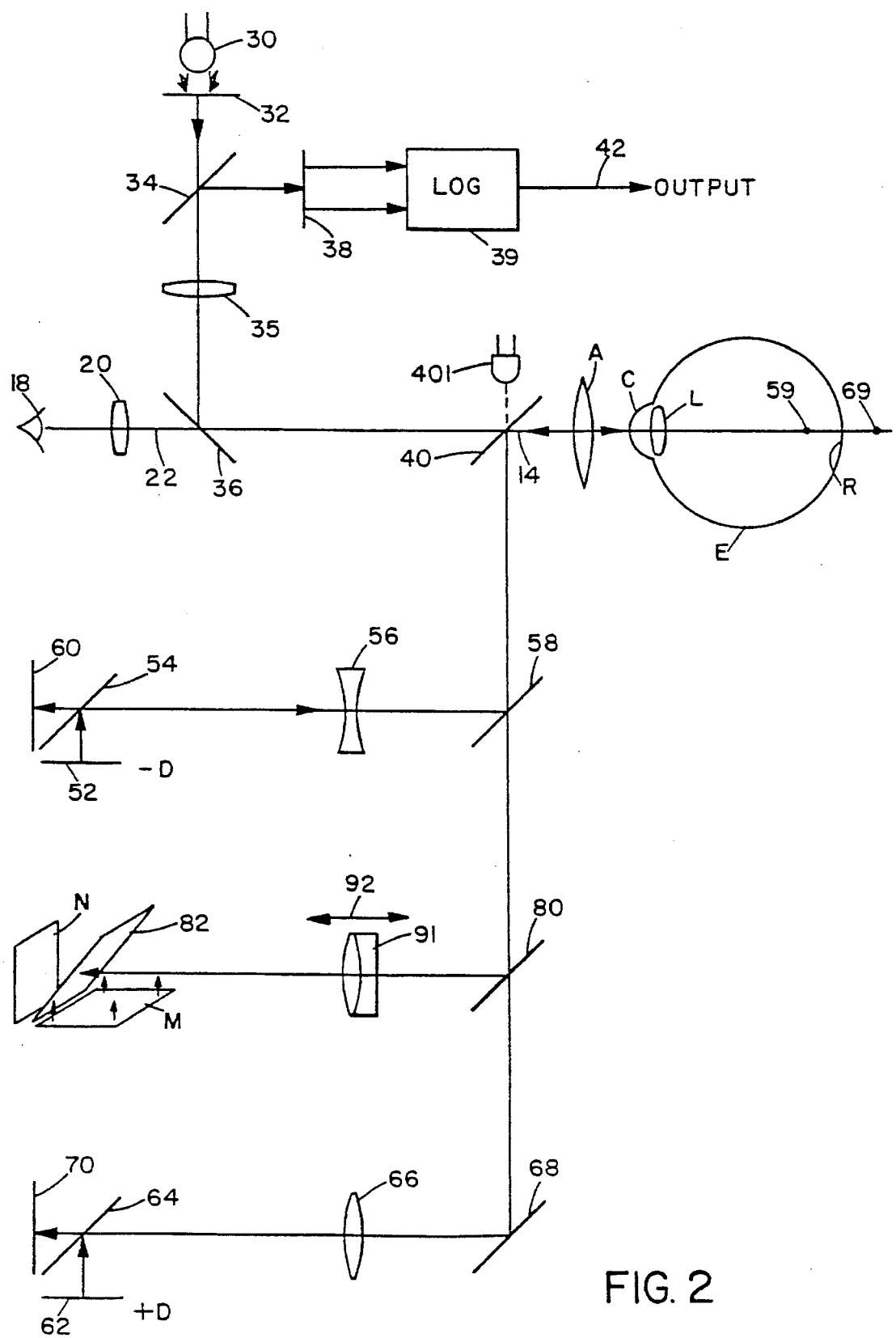
FIG. 2 is an optical schematic of the autorefractor of an embodiment of the invention.

The schematic of another alternate embodiment is provided in FIG. 2. Instrument I includes an interrogating eye path 14 to and from eye E of patient P (not shown except at eye E in FIG. 2). This interrogating eye path 14 is the route that all light paths to and from the instrument follow between instrument I and patient's eye E.

Light path 22 is provided to allow an eye examiner E to look to and from patient's eye E. This light path functions to produce the required gross alignment of instrument I to eye E.

It should be noted that the disclosed optics and recording electronics are operable when the eye is grossly aligned. However, in the preferred embodiments of this invention, precise eye alignment can be utilized. For such alignment, a Purkinje imaging system may be utilized.

Light source 30 for a conventional Purkinje image is produced at slide 32. Typically, light from source 30 is within a discrete color band (for example green) passes through beam splitter 34, lens 35 and is deflected by beam splitter 36 to interrogating light path 14. Lens 35 functions to focus Purkinje image to cornea C and lens L of eye E. Additionally, visible to the eye examiner is the first Purkinje image, which assists in grossly aligning the instrument with the subject's eye. The first Purkinje image can also be used for tracking direction of gaze since the image reflected from the cornea will move with the eye.

Generation of the Purkinje images is known in the art. Specifically, these respective images are generated from the surface of the cornea C (most intense image), from the front surface of eye lens L (substantial reduced image), and finally from rear surface of eye lens L (extremely faint image). Light from the respective Purkinje images is retro-reflected through hot mirror 40, which is transparent to visible light, and diverted at beam splitters 36 and 34 to detector 38. Detector 39 outputs to log circuit 39 (or similar compression circuit) and finally to output 42.

Log circuit 39 is provided to compensate for the differences between the various images, which can be several orders of magnitude. Further, when all signals are aligned, log circuit 39 outputs at 42 a maximum signal which indicates that the instrument I is correctly aligned to eye E for refraction. When using a multiple-segmented photodetector array with the Purkinje image sensor can determine whether only one segment (indicating coincidence of the three images) has a signal or whether more than one segment (indicating non-coincidence and non-alignment) have signals.

The above described Purkinje system is an auxiliary device and may not be needed. It is used at only a close distance to the eye, about 2 to 6 cm range. The "gross alignment" or "centered" relationship does not require precise alignment. In contrast with the first embodiment, the measurement beam overfills the pupil so that if the eye not perfectly "centered" the patient can still fully see the target, and when the patient looks at the target the optical axis of the instrument and of the patient's eye are "perfectly" aligned.

For the second embodiment, all that is required is that the patient's eye appear in the examiner's field of view (through the instrument eyepiece). Because there are many measurement pulses per second, the patient need only momentarily fixate the target to get the refraction. Indication that the eye is aligned, even momentarily, is also signaled by outputs from across $R_{lim}$ 123 and the outputs of +diopter and –diopter background (diffuse light) amplifiers 102 and 103 shown in FIG. 4. These outputs are stored and compared for each measurement pulse. Relative differences between these outputs indicate whether the eye is accommodating or not (in accommodation the pupil becomes smaller thereby changing diffuse light from the eye) and whether the eye looking most directly at the fixation target (best alignment means strongest retro-reflection of images so that emitter current and output across $R_{lim}$ is a minimum). It should be noted that the Bruckner Effect, which reduces reflected light, is not operative in this application, because, among other reasons, the projected image is a disc rather than a point source.

In the second embodiment, the Purkinje image sensor does not follow the eye, but only indicates when the optical axis of the eye is aligned or nearly aligned (looking at the fixation target) with the instrument's optics. (Provisions must be made for tracking the Purkinje image sensor when it is used for determining direction of gaze.)

A further application of the Purkinje image sensor is to determine that the patient's eye is within measuring distance and properly in place. When the eye not within distance or not in place, there is no return signal. When there is a return signal (return signal produced at virtually same time as emitted signal) a simple AND logic indicates that an eye is in place and within the power and optics of the instrument. This corresponds to the vertex range sensor of the first embodiment.

The output across $R_{lim}$ 123 can also be used as a vertex sensor, the output being a maximum when the eye is not in place or the vertex is beyond measurement range, and the output of $R_{lim}$ becoming less as the vertex distance decreases.

Referring again to FIG. 2, a first signal D is emitted from emitter 52 in the form of a target image for transmission to eye E. This signal passes through negative lens 56 for reflection at beam splitter 53 and then for reflection from hot mirror 40 and through optometer lens "A" onto interrogating eye path 14. Taking the case of an emmetrope, negative image 69 is beyond retinal plane R. Lens "A" acts as a conventional optometer lens to produce converging rays when the image source is at a focal length greater than that of the optometer lens, and diverging rays when the image source less than that of the optometer lens' focal length. The "negative" and "positive" lenses merely shorten the optical path.

The return light path is analogous. Light from image 69 (on the retinal plane R) returns through reflection from the hot mirror 40 and beam splitter 58, and finally passes through beam splitter 54 onto detector 60.

Referring again to FIG. 2, a second signal D+ is emitted from emitter 62 in the form of a target image for transmission to eye E. This signal reflects at beam splitter 64 and passes through positive lens 56 to mirror 68 and then through beam splitters 80, 58 to reflection at hot mirror 40 and onto interrogating eye path 14. Taking the case of an emmetrope, negative image 59 is short of retinal plane R.

The return light path is analogous. Light from image 59 (on the retinal plane R) passes through optometer lens "A" and returns after reflection at the hot mirror 40, passes through beam splitters 58, 80, and reflects from mirror 68, passes through beam splitter 64 and onto detector 70.

Having set forth the light paths, and assuming that the pupil of eye E does not dilate, the intensity of the respective signals can be observed with respect to FIGS. 3A–3F, which have been previously discussed.

A significant problem in producing a ratio between the respective signals is that the eye under examination can dilate. In the case of such dilation, the ratio between the respective signals 79, 89 can change. In order to prevent such a change in ratio, the circuitry of FIG. 4 is utilized.

Figure 4:
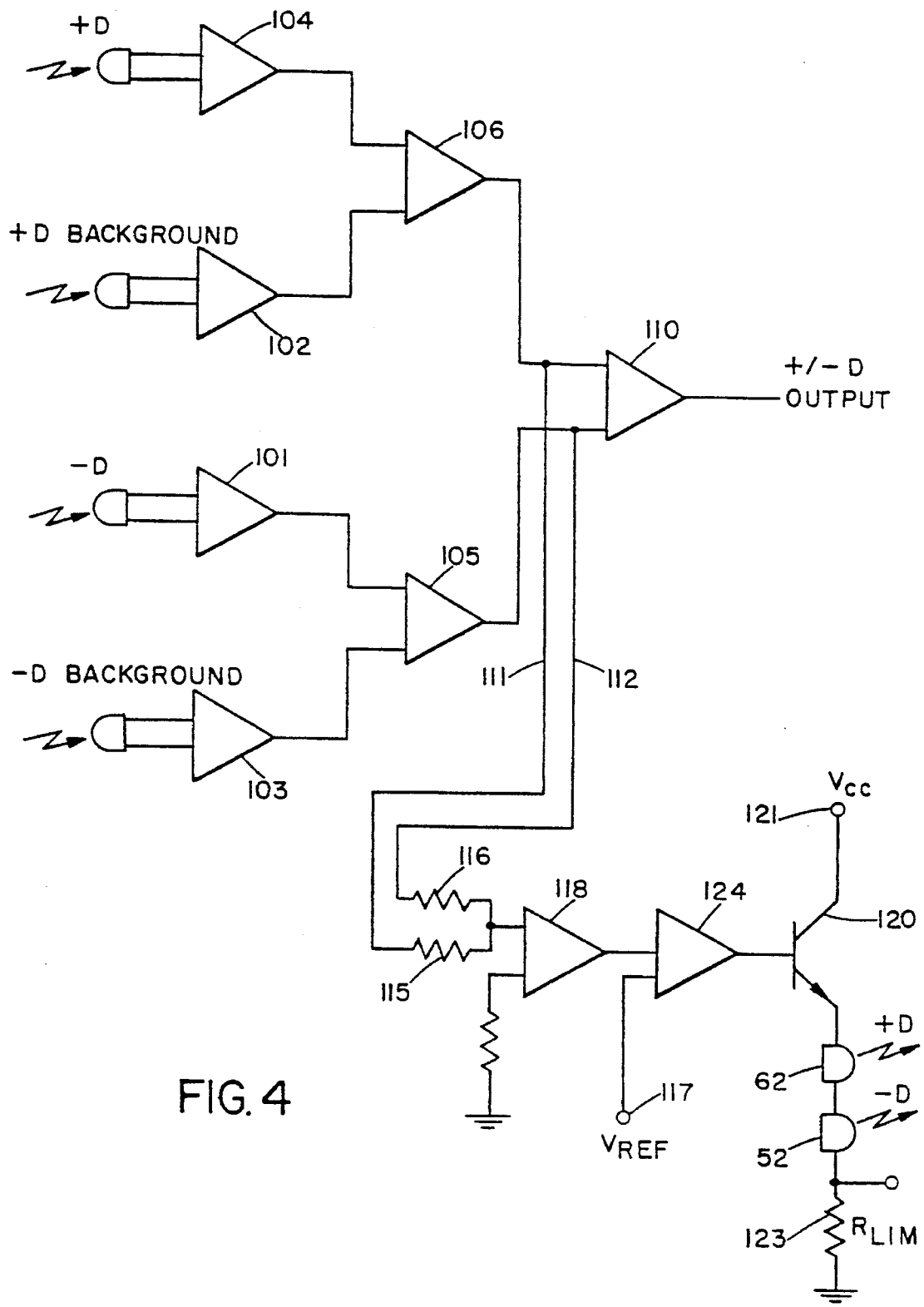
FIG. 4 is a schematic of the differential circuitry of an embodiment useful for determination of gross overall sphere with a constant proportion of signal despite dilation of the examined eye.

Referring to FIG. 4, the first portion of circuitry is conventional. Respective background signals from detectors 60 and 70 and respective image signals from spots 59, 69 are routed through amplifiers 101–104 and to summing amplifiers 105, 106. The respective outputs of amplifiers 105, 106 are routed to a differential amplifier 110. Differential amplifier 110 outputs a voltage which is directly proportional to the difference in image intensity. By way of example, a negative voltage can indicate myopia and a positive voltage can indicate hyperopia.

The case of eye E of patient P dilating is set forth in the ancillary circuitry illustrated. Specifically, total signal to comparing amplifier 110 is monitored by respective lines 111, 112. These pass to summing resistors 115, 116 to one input of summing amplifier 118, and the output of summing amplifier 118 goes to the input of current control amplifier 124. The other input of current control amplifier 124 comes from reference voltage input 117. This illustrative current control (clamping) circuit can be replaced by a ratiometric circuit which eliminates the reference voltage, or similar circuit to achieve the same purpose.

Dependent upon total intensity of signal received from both images, output of signal from the current control amplifier 124 goes to the base of transistor 120. Transistor 120 serves to control current from current source 121. Current passes through respective light sources 62, 52 and finally through a limiting resistor 123 and then to ground.

Presuming that eye E at the pupil contracts, less signal will be seen at amplifier 124 relative to reference voltage 117. This being the case, the base of transistor 120 will open to permit a greater flow of current through light sources 52, 62. When a greater current flows through the respective light sources 52, 62, the intensity of signal received at amplifier 124 will increase until an equilibrium condition is established. The respective output signal at amplifier 110 will remain essentially in the same ratio and will not be affected by eye dilation.

In the case of pupil contraction is the opposite with total current flow through the respective light sources 52, 62 being reduced. Numerous other schemes can produce the required normalization of the signal ratios in the presence of eye dilation.

The embodiments of the inventive auto refractometer may be used for topographical mapping of the retina or other detailed analysis thereof. This is possible because different points on the retina can be refracted and refraction correlates to distance to/from the eye's optics, that is, a topological map. By using two wavelengths, for example, green (red-free light) and red (near-infrared), the surface and subsurface features of the retina can be mapped. This data could be input to a neural network for objective and automatic detection of various eye diseases.

An immediate application of the invention in surgery can be locating areas of macular edema. Techniques are being developed for subretinal drainage.

A topological mapping instrument of this nature might help understand the eye better and enable further advances in ophthalmic surgery. Furthermore, sets of data input to a neural net might be classified to reveal a method to recognize and diagnose incipient glaucoma.

For the topographical mapping function, images projected to the fundus must be kept precisely in alignment. Accordingly, use of the Purkinje imaging system is used as follows.

In the first embodiment, an interactive optics system tracks the direction of eye gaze using the first Purkinje image (reflected from the cornea) and measures the length of gaze with the autorefractor function. (Length of gaze simply involves measurement of refraction during accommodation to focus on an object at a given distance, either actual or projected, from the viewer. Once the refraction is measured, the distance at which the eye is focused can be determined.) Using virtual reality techniques to project images at near and distant positions, the inventive system, using a CCD imager as the detector, can test for defects of refractive defects, strabismus and amblyopia.

By knowing the direction and length of gaze, many instruments can be reduced to a combination of goggles (or a virtual reality helmet) and a laptop computer. This would allow many vision tests to be performed, including those listed above, which are often difficult to conduct on children.

Another application is perimetry which can be accurately determined once the length and direction of gaze is known. Direction of gaze enables accurate mapping, limited, of course by the accuracy of the tracking system, while length of gaze ensures that projected stimulus points are actually imaged onto the retina.

By using a laptop computer to control the perimeter, interpretation of the mapped visual field is possible for use in preliminary diagnoses. This provides a portable system which allows for automatic and objective screening for diseases at greatly reduced expense, with minimal training required for operation.

Another application of the autorefractor with a CCD imager is to capture the image of the fundus, then display it on a color LCD screen, thus enlarging the image that must be viewed by the examiner. This facilitates selection of the appropriate lens focal length to bring the retina into sharp focus on the CCD and then allows a record of the image of the retina to be stored for later analysis, either by computer or for review by the examiner, to look for, among other things, the seven criteria discussed below.

By using the autorefractor function in combination with a CCD imager, which can replace the photodiodes in all embodiments, and the Purkinje image sensor for tracking, sharp images of the fundus can be generated. Normal and abnormal images can be distinguished by analyzing the images for the following seven criteria: 1) sharpness of optical disc, 2) symmetry, 3) color, 4) ratios of veins to arteries (by using two different light colors (green and red) veins and arteries can be differentiated), 5) continuity of veins and arteries, 6) continuity of colors, and 7) continuity in lens/vitreous.

In addition to testing the above seven criteria, fundus images can be correlated with the visual field map to aid clinical diagnosis. A method for analysis of retinal images in a system with a CCD imager includes generating an image of the imaged fundus, then dividing the fundus into quadrants. Alternatively, a number of discrete optic discs can be generated.

A fast Fourier transform (FFT) is performed for each quadrant or discrete disc using images generated using blue, green and red light by using dichroic filters with the CCD imager. A number of sets of FFTs should be obtained, on the order of 12 to 15, for each of the quadrants or discrete discs, for the subject eyes, for normal eyes and for each type of eye disease to be considered. The subject's data sets should be compared, possibly using a neural network set up to classify the input data according to the normal and abnormal standards. The entire retina can be scanned by taking images with the subject looking straight, up, down, right and left, with the computer fitting the images together in a mosaic. Since the subject's refraction is known, focus can be varied within the range from the retina to the cornea to find vitreous defects or cataracts.

Referring to FIG. 2 for the second embodiment, a matrix E of light sources reflects from beam splitter 82, and reflects at beam splitter 80 onto interrogating optical path 14. At interrogating optical path 14, image adjustment of the image of matrix M is made by lens movement of lens 91 towards and away from eye E along path 92. The purpose of a movable lens is merely to allow greater resolution, that is, to map many discrete points: Matrix M must project discrete discs that may be blurred on the retina, but not so blurred that the projected discs on the retina overlap. The topological profile corresponds to the photodetection measurement on the photodetector array N. In the case of obtaining an image of the fundus using a CCD, lens movement enables high resolution of the fundus.

In this embodiment of the invention, the measure aperture overfills the pupil of the eye. In order for accurate measurements to be taken, it is only required that the eye be within the range of the instrument within relative rough limits. These rough limits can be determined by another embodiment of a vertex range sensor.

Figure 6A:
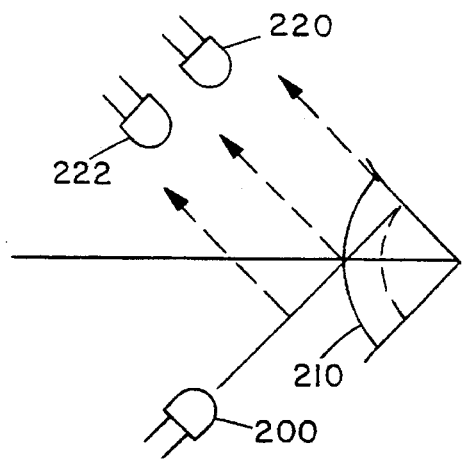
FIG. 6A is an optical schematic and FIG. 6B is an electrical schematic for the vertex sensor of an embodiment of the invention.
Figure 6B:
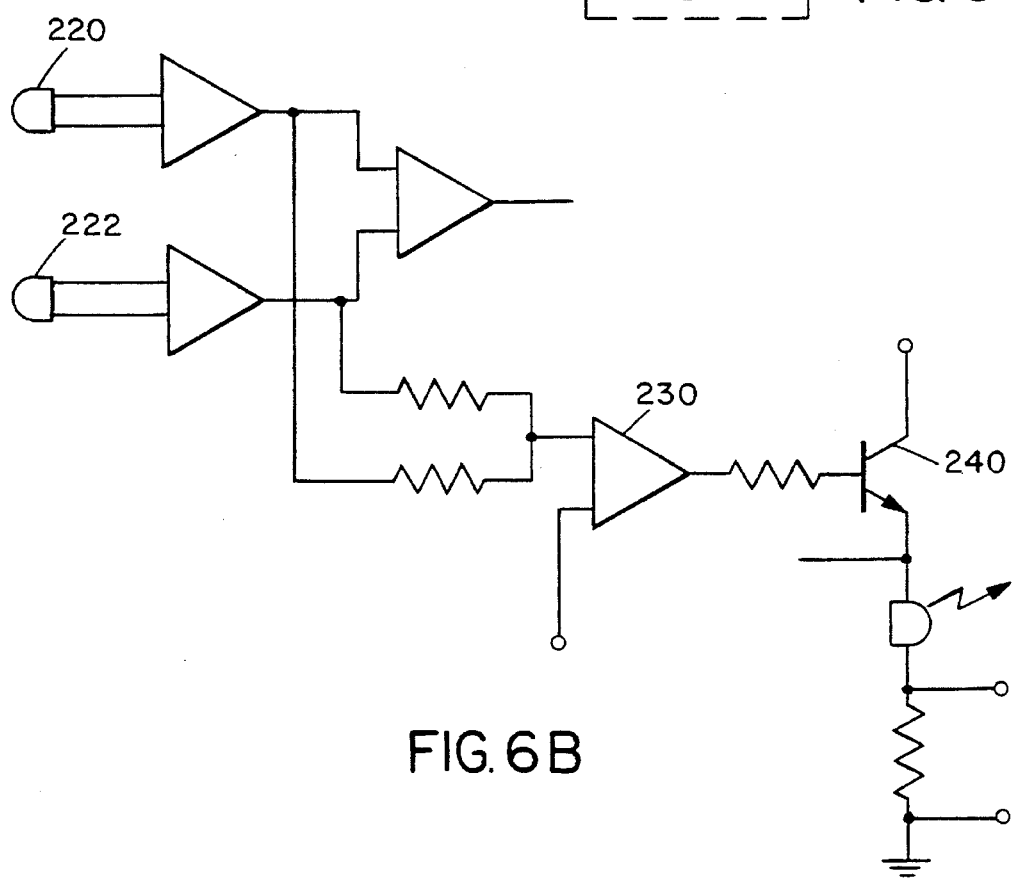

Referring to FIG. 6A, a single emitter 200 (IR) projects a beam onto the eye's cornea 210 as shown. This is essentially the same as a number of other similar devices for finding distance. The main difference in this arrangement is the electronics of FIG. 6B: the two inputs 220, 222 (photodetector signals) are summed together at amplifier 230 and the emitter current 240 increases or decreases to maintain a constant sum of the two inputs. This means that the resulting voltage from the detectors' electronics is proportional to vertex distance. And this voltage can be used to make corrections in diopter measurement caused by varying eye distances from the instrument optometer lens, if such correction be required. This arrangement of +D and −D signals will make the eye measurement less sensitive to changes in vertex distance.

Figure 6C:
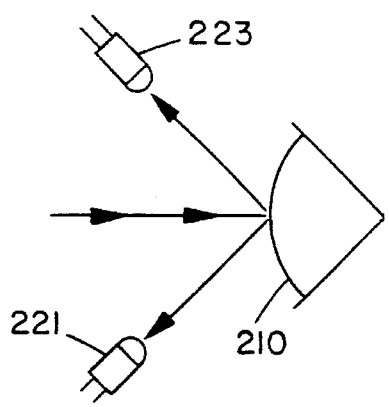
FIG. 6C is an optical schematic of the vertex sensor with two photodiodes and FIG. 6D is an optical schematic of the vertex sensor with two pairs of photodiodes.

The vertex sensor illustrated in FIG. 6C uses the measurement beam and has only two photodetectors 221 and 223. The vertex photodiodes 221 and 223, as well as 221' and 223' in FIG. 6D, have a narrow view angle, and are signified in the figure as long, narrow detectors, indicating lensed photodetectors.

Any reflection that is very far away from the axis of the vertex photodiodes will not be detected. Further, the intensity of the measurement beam is fixed, so that when the eye is located within the measurement range of the vertex sensor, and the eye is properly positioned between the photodetectors 221 and 223, the outputs of the two detectors will be approximately equal and both outputs will be above a previously (empirically) determined intensity level.

Figure 6D:
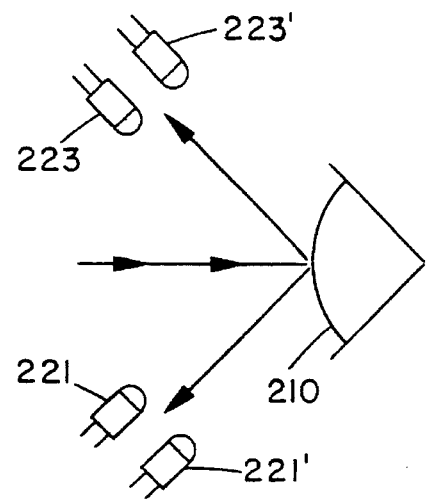

The vertex sensor illustrated in FIG. 6D uses the measurement beam which has fixed intensity and two pairs of lensed, narrow-angle photodiodes (221,221', 223, and 223'). When the eye is within the measurement distance of the autorefractor, the outputs of each pair of detectors (221/221' and 223/223') will be approximately equal regardless of the intensity of the measurement beam.

Assuming correct alignment of instrument I at interrogating optical path 14 to eye E, the auto refraction can now occur. In explaining the requisite auto refraction, the case of an emmetrope will first be considered. With reference to FIGS. 3A–3F, the reception of signals from the eye are illustrated. In FIG. 4, a circuit for outputting a voltage proportional to prescription at the eye E is shown.

Figure 5B:
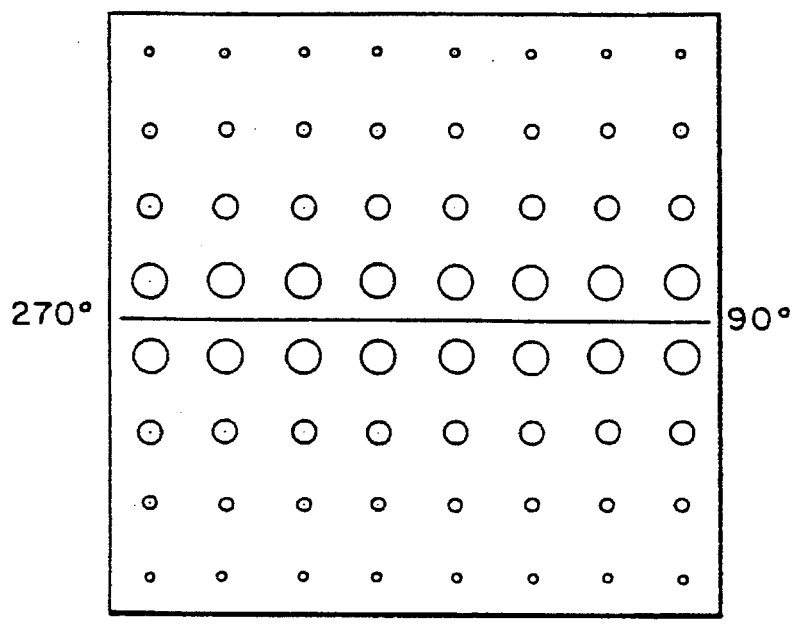
FIG. 5B is an intensity diagram of the eye where a patient has astigmatism along a 90 degree axis, the astigmatism here being illustrated in the range of positive one half of a diopter.
Figure 5A:
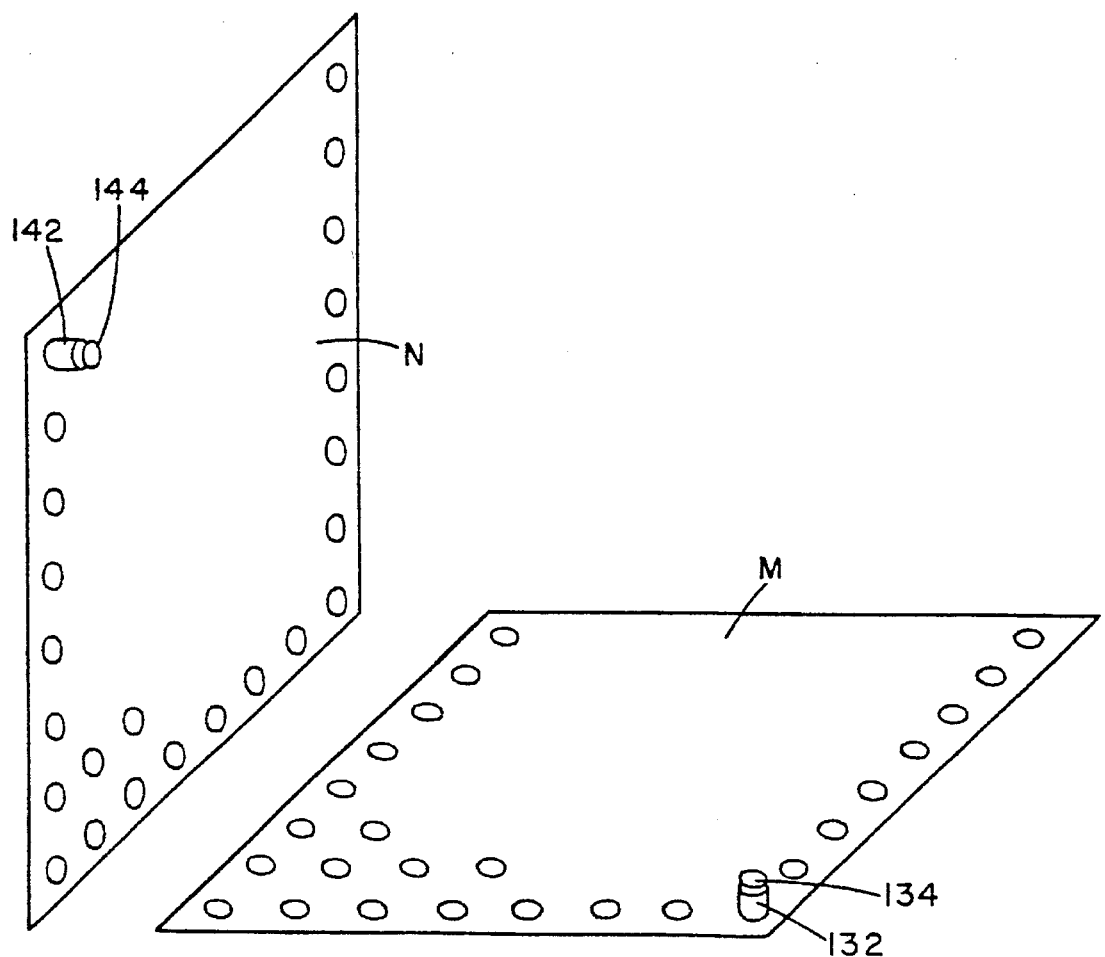
FIG. 5A is a schematic for the projection of an image registered to the eye.

Referring to FIGS. 5A, image matrix M includes an 8 by 8 light source array—such as low-intensity microlasers 132 passing through corresponding micro lenses 134. These respective light sources 132 and lenses 134 are given respective focal lengths so that the matrix of light sources projects to retinal plane R on eye E.

The received image is analogous. Respective detector segments 142 receive through corresponding micro lenses 144 images from retinal plane R of eye E. The respective projecting matrix M and receiving array A are registered, one to another. In this way, an element of receiving array P overlies a corresponding element of projecting matrix M.

Referring to FIG. 5B, the respective results of such an image are projected. Specifically, it will be remembered that the spherical portion of this invention observes gross sphere only; thus far astigmatism has been ignored.

Referring to FIG. 5B, the resultant image received at array A is shown projected—as at a conventional CRT. Amplification of the respective matrix locations is shown graphically in increased size at each matrix position. As shown, the patient P includes positive sphere along the indicated 90° axis.

Mean sphere error and +/− diopter error is obtained from the main diopter measuring circuits, cylinder and axis may be obtained by one of the following three methods.

The first method is by using a fixed detector array (microlenses and photodetectors) to find meridional refraction (points around the optical axis) and these refractive measurements used in either Lawrence's formula (remembering that +/− diopter sphere is already given: Immediately finding +/− diopter sphere is a significant difference compared to conventional meridional refractometry), or using a curve fitting program to find the best curve to correct for astigmatism. In theory, this method can perfectly correct for astigmatism, even irregular astigmatism, because the resulting corrective lens could be computer-ground to perfectly match all the various meridional refractive measurements on the microlens detector array.

A second method is measuring the elliptical distortion of the projected circular disc. The amount and direction of the elliptical distortion correlates to meridional refraction and provides at least three axes to plug into Lawrence's formula, or remembering that +/−D sphere already found, a curve fitting program or solution of equations known to give cylinder and axis.

A third method detects the distortion of a retro reflected circular pattern and measures the orientation of distortion to find axis, and measures ratio of length-to-width and then uses a simple look-up table to find cylinder. Each of these methods is similar to those described for the first embodiment with the exception that, in the first embodiment, the image is simply a projected spot rather than being a matrix of spots.

It should be noted that only the illumination pattern of a matrix is illustrated and that other techniques can be utilized. For example, elliptical distortion might be detected by an array of meridional photodetectors located at the −D photodetector position, e.g., a multi-segmented photodiode. The important concept is that operation of this embodiment of the inventive refractor, gross sphere is first determined then used to examine for cylinder and axis.

Figure 7A:
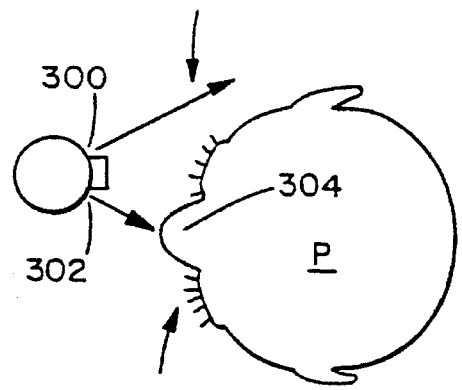
FIG. 7A is a plan view of a patient utilizing left and right eye sensors shown sampling the face of the patient during examination of the right eye of the patient.
Figure 7B:
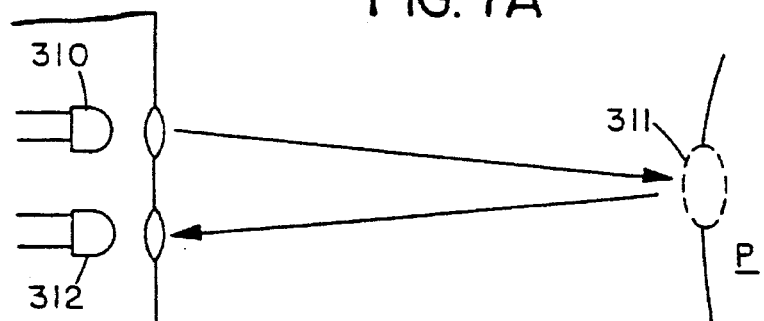
FIG. 7B is an expanded side elevation section of a light source and sensor.
Figure 7C:
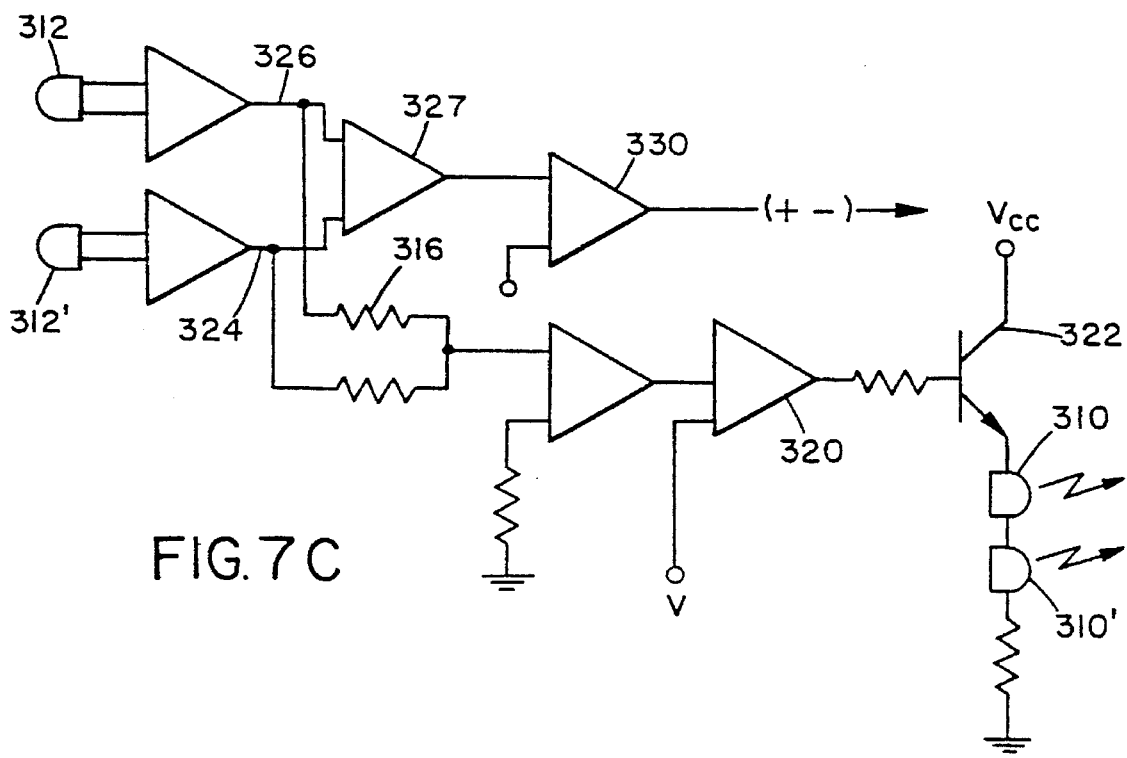
FIG. 7C is a circuit for comparing the respective views of the patients face for indicating the particular eye of the patient examined as well as the general proximity of the instrument to a patient.

Referring to FIGS. 7A–7C, an embodiment of the refractor is set forth in which the eye of a patient is indicated—left or right—during the examination of a patient P. This device enables the particular measurement to be correlated with the eye examined and enables comparison to a corresponding measurement of the other eye which is particularly useful in identifying amblyopia.

Referring to FIG. 7A, emitter/receptor pair 300 sends out a signal that is not reflected during examination of the eye of a patient P. Emitter/receptor pair 302 sends out a signal that is reflected during examination of the eye of a patient P.

Referring to FIG. 7B, one of the emitter/receptor pairs 300, 302 is illustrated. An emitter 310 projects a beam 311 on the nose of patient P and a return signal is registered at receptor 312.

Referring to FIG. 7C, photosensors 312 for left eye and 312' for the right eye are illustrated. Outputs 324, 326 are routed to summing resistors 316 and thereafter to amplifier 320. Dependent upon the strength of the signal received, transistor 322 passes current through respective light sources 310 for the right eye and 310' for the left eye. Where the signal is faint, the respective light sources 310, 310' operate at full intensity. Where the signal is strong, output through amplifier 320 is reduced and current through respective light sources 310, 310' is reduced.

Determination of the particular eye being examined will be made through comparison amplifier 327. Where left eye 312 sensor has the predominating signal, a positive voltage will be output through amplifiers 327, 330. Where right eye 312 sensor has the predominating signal, a negative voltage will be output through amplifiers 327, 330. Thus, by the polarity of the signal utilized, determination of the particular eye examined can be made. By coupling the polarity of the signal to the measurement taken, measurements of each eye can be tagged and examined for disparities evidencing amblyopia.

It will be noted that because the circuit is comparative, whether a person of dark or light pigmented skin is examined is of no matter. Presuming that the respective detectors are in gross range of a patient and pass the respective preset thresh holds of amplifiers 32D, 330, a signal indicating left or right eye examination will be emitted from amplifier 330.

Subsequently, refractive measurements can be categorized as to right eye and left eye. When the refractive readings are sufficiently disparate or when both refractive readings indicate poor eyesight, the instrument alerts the eye examiner to further examine the patient for possible amblyopia.

Provision is made for auto calibration of the instrument at the beginning of each measurement sequence to ensure extreme linearity and zero-drift long term stability. It should be noted that auto calibration can be obtained in a variety of ways and that this method is merely illustrative.

Referring to FIG. 2, photodetector 401 is located in the path of −diopter emitter 52 and +diopter emitter 62. The location of 401 could also be at beam splitter 58 or other similarly positioned location. Because hot mirror 40 "leaks," or can be designed to leak 1% or so of the emitter beam, photodetector 401 can measure optical output from the −diopter and +diopter emitters.

A series of calibrated pulses alternately pass through each emitter so that either a correction factor can be applied to one or both emitters to make the optical outputs equal for a given calibrated emitter current or a correction factor can be incorporated in signal processing of the detected retro reflected signals. A particular advantage of this method, beyond enabling extreme linearity and zero-drift stability, is to provide more "calibration marks" at the extreme ranges of the diopter scale for greater accuracy.

Having set forth the embodiments of the invention, it can be seen that numerous advantages are realized. These include:

a) Very short pulses stop the motion of the eye while allowing many measurements to be taken for averaging to improve accuracy;

b) Random noise is reduced by the square root of the number of valid measurements, that is, if 49 valid measurements, the signal-to-noise ratio is improved by seven times;

c) Low average power yet high peak optical power output, e.g., if a component is rated at 1 milliwatt but has a duty cycle of 20%, the peak power could be increased five times to 5 milliwatts;

d) Because of low average power and high peak output, tiny components can be used in the instrument. To increase power rating and for longer life, heat sinks can be employed. In any case, the instrument for each patient will be used only for a few seconds;

e) Low power consumption enables an entirely self-contained, battery-powered instrument;

f) Small size of the instrument means that it is palm-size and entirely self-contained. The instrument casing can be injected molded in two halves with the optical and electronic components fitting into preformed mounts or slots. Equally important, however, is lower cost of manufacture (smaller and fewer components), lower distribution cost (ship by mail), and lower service costs (replace instrument via express mail);

g) Fixed optical system with no moving parts;

h) Photodetectors have high quantum efficiency and are lensed for high sensitivity;

i) Optical and electronic filters suppress ambient light;

j) Dichroic beam splitters increase efficiency of light path;

k) Relatively high optical output of LED measurement signal strength (less, however, than a standard ophthalmoscope so that use is entirely safe);

l) Very sensitive photodetector amplifier with input bias around 1 pA or less, and stability in microvolts;

m) Internal instrument light ("glare") suppressed by optical and electronic means;

n) The two main diopter measuring signals must remain constant under changing signal strength (pupil dilating/contracting, retinal pigmentation, etc.) because the ratio of these two signals correlates to refraction. (In the case of CCD photodetectors, the ratios of the blur circles are used as previously described.) To achieve this:
  1) (Signal of +D emitter)+(Signal of −D emitter)= constant (fixed) voltage; or,
  2) (Signal of +D emitter)=(Signal of −D emitter) and (Signal+D)−(Signal−D)=constant (fixed) voltage.
  The "constant (fixed) voltage" can be set at 5 V, or any other voltage that satisfies the circuitry and formula 1) or 2);

o) Background noise (diffuse light) is subtracted from the main diopter signals:
  1) off-axis photodiodes detect the diffuse light.
  2) corneal reflection determined using multi-segmented photodiode or CCD imager can be subtracted.
  3) Instrument glare suppressed optically, but with output from across the R limiter of the diodes this glare can be subtracted (eliminated) from the main diopter signals because with higher (lesser) signal output and more (less) glare the R limiter voltage will be higher (lesser);

p) Vertex range makes the instrument automatic for close (or one meter) measurements: The instrument will not start producing measurement pulses unless the instrument is within proper vertex distance. This circuit is different from other similar appearing circuits because a voltage that corresponds to vertex distance is produced, and this voltage can be used for minor corrections in the refractive readings;

q) Diffuse light levels change to indicate maximum iris opening and closure to indicate minimum accommodation (the pupil becomes smaller upon accommodation);

r) Purkinje image sensor detects when the first and second images (from a separate, visible green LED) are coincident. This is an auxiliary sensor for close-up refraction and ray used where required;

s) Data storage records all the "valid" measurements;

t) By using the signals 1) generated across $R_{lim}$ of the emitters and 2) background (diffuse) light detectors, alignment/minimal accommodation can be determined because 1) voltage across $R_{lim}$ is at a minimum when the eye is unaccommodated (accommodation causes the pupil of the eye to contract when the ciliary body pulls on the lens to shorten the lens' focal length);

u) A variety of electronic circuits can be configured to obtain the output function (S1−S2)/(S1+S2) and the corresponding eye refraction. Applications of the inventive autorefractor, in addition to those identified above, include measurement of refraction at locations remote from an opthalmologist's or optometrist's office, for example, on-site testing at schools, use in experimental settings, such as in the Space Shuttle or in flight or space simulators. In addition, refractive testing can be performed on animals by veterinarians, who often need to make "house calls" to care for larger animals. The advent of laser refractive surgery to correct myopia (laser keratotomy) will require autorefractors mounted in surgical microscopes to monitor the progress of laser surgery. The small size of the present invention makes it ideal for such an application.

Current virtual reality technology is limited by problems such as the difficulty in determining where the user's eyes are focused. For example, even though a scene may be presented as being close-up, the viewer's eye may not actually be focused on the nearby objects. Also, when an object is approaching the viewer, although the viewer has binocular vision of the approaching object, the object may not be perceived by the eye's accommodating mechanism as getting closer. This causes confusion in the brain's vision centers, causing nausea and headaches.

The VR processor can work interactively with an autorefractor according to the present invention by providing information about the viewer's length of focus, so that the scene being fixated by the eye can be brought into correct focus. These interactive optics can help reduce the vertigo and headaches associated with current VR technology.

It will be evident that there are additional embodiments which are not illustrated above but which are clearly within the scope and spirit of the present invention. The above description and drawings are therefore intended to be exemplary only and the scope of the invention is to be limited solely by the appended claims.

I claim:

1. In an interactive virtual reality imaging system, a process for determining length of focus of an eye of a system user for adapting focus of an image generated by the imaging system, wherein said eye has a lens, a cornea and a retina, the process comprising:

identifying an optical path to the retina of said eye;

projecting a first image along said optical path to the retina of said eye, said first image being focused at a first focal point along said optical path beyond the retina of said eye;

detecting said first image from said optical path reflected from the retina of said eye and generating a first signal proportional to an intensity of said first image;

projecting a second image along said optical path to the retina of said eye, said second image being focused at a second focal point along said optical path in front of the retina of said eye;

detecting said second image from said optical path reflected from the retina of the eye and generating a second signal proportional to an intensity of said second image;

comparing said first and second signals for indicating a relative intensity of said first and second images to determine an accommodation of said eye to provide the system user's length of focus; and adjusting the focus of the image to correspond to the user's length of focus.

2. The process of claim 1 further including tracking a gaze direction of the system user, comprising:

projecting a Purkinje image along said optical path focused in a vicinity of the cornea of said eye;

receiving a reflected Purkinje image at least from the cornea of said eye along said optical path; and comparing alignment of the projected Purkinje image with the reflected Purkinje image.

3. The process of claim 1 wherein each of the steps of detecting the first and second images comprise detecting with a multi-segmented photodiode.

4. The process of claim 1 wherein each of the steps of detecting the first and second images comprise detecting with at least one CCD imager.

5. In an interactive virtual reality imaging system, a process for focusing a scene created by the system with a length of focus of an eye of a system user, wherein said eye has a lens, a cornea and a retina, the process comprising:

identifying an optical path to the eye;

projecting a first image along said optical path to the retina of said eye, said first image being focused at the retina of said eye;

detecting said first image from said optical path reflected from the retina of said eye with a first detector having a focus corresponding to a first focal point along said optical path beyond the retina of the eye and generating a first signal S1 proportional to an intensity of a first reflection of said first image;

detecting said first image from said optical path reflected from the retina of said eye with a second detector having a focus corresponding to a second focal point along said optical path in front of said retina and generating a second signal S2 proportional to an intensity of a second reflection of said first image;

comparing said first and second signals according to the relationship $(S1-S2)/(S1+S2)$ to determine accommodation of said eye to provide the system user's length of focus; and adjusting the focus of the scene to correspond to the user's length of focus.

6. The process of claim 5 further comprising the steps of:

projecting a second image along said optical path focused in a vicinity of the cornea of said eye;

receiving a reflected second image from the cornea at at least one detector; and comparing alignment of the incident and reflected second images to determine the system user's directions of gaze.

7. The process of claim 6 wherein said at least one detector comprises two detectors, each detector generating an output signal and further comprising the steps of:

summing the output signals of the two detectors; and providing a signal when the sum of the output signals varies from a preselected constant to indicate improper alignment.

8. The process of claim 6 where said second image is a Purkinje image.

* * * * *